(12) United States Patent
Ashrafzadeh et al.

(10) Patent No.: US 9,353,475 B2
(45) Date of Patent: *May 31, 2016

(54) LAUNDRY TREATING APPLIANCE WITH FLUFFING-STATE DETECTION

(71) Applicant: Whirlpool Corporation, Benton Harbor, MI (US)

(72) Inventors: Farhad Ashrafzadeh, Bowling Green, KY (US); James P. Carow, Saint Joseph, MI (US); Layne E. Heilman, Osceola, IN (US); Shreecharan Kanchanavally, Naperville, IL (US)

(73) Assignee: Whirlpool Corporation, Benton Harbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/470,994

(22) Filed: Aug. 28, 2014

(65) Prior Publication Data

US 2014/0366398 A1    Dec. 18, 2014

Related U.S. Application Data

(62) Division of application No. 12/388,773, filed on Feb. 19, 2009, now Pat. No. 8,832,966.

(51) Int. Cl.
*F26B 3/02* (2006.01)
*D06F 58/28* (2006.01)
*D06F 33/02* (2006.01)
*D06F 39/00* (2006.01)
*G01N 21/55* (2014.01)
*D06F 58/02* (2006.01)
*D06F 58/20* (2006.01)

(52) U.S. Cl.
CPC ................ *D06F 58/28* (2013.01); *D06F 33/02* (2013.01); *D06F 39/003* (2013.01); *D06F 58/02* (2013.01); *D06F 58/203* (2013.01); *G01N 21/55* (2013.01); *D06F 2058/289* (2013.01); *D06F 2058/2829* (2013.01); *D06F 2058/2841* (2013.01); *D06F 2058/2861* (2013.01); *D06F 2058/2896* (2013.01); *D06F 2204/065* (2013.01)

(58) Field of Classification Search
CPC ................ D06F 58/28; D06F 2058/28; D06F 2058/2816; D06F 2058/2841; D06F 2058/2861; D06F 2058/2877; D06F 2058/289; D06F 2204/065; D06F 58/02; D06F 58/203; D06F 2058/2829; D06F 2058/2896; G01N 21/55; F26B 3/02
See application file for complete search history.

(56) References Cited

U.S. PATENT DOCUMENTS 7,066,412 B2 *   6/2006   Conley et al. ................ 239/690
8,832,966 B2 *   9/2014   Ashrafzadeh ........... D06F 33/02
                                                                    34/491

FOREIGN PATENT DOCUMENTS

JP              05200194 A  *  8/1993

* cited by examiner

*Primary Examiner* — Jiping Lu

(57) ABSTRACT

The invention relates to a method of determining a fluffing state of laundry based on a determined temperature indicative of the surface of the laundry.

12 Claims, 6 Drawing Sheets

LAUNDRY TREATING APPLIANCE WITH FLUFFING-STATE DETECTION

CROSS-REFERENCE TO RELATED APPLICATIONS

The present application represents a divisional application of U.S. patent application Ser. No. 12/388,773 entitled "LAUNDRY TREATING APPLIANCE WITH FLUFFING-STATE DETECTION" filed Feb. 19, 2009, currently allowed.

BACKGROUND OF THE INVENTION

Laundry treating appliances, such as clothes washers, clothes dryers, refreshers, and non-aqueous systems, may have a configuration based on a rotating drum that defines a treating chamber in which laundry items are placed for treating. The laundry treating appliance may have a controller that implements a number of pre-programmed cycles of operation. The user typically manually selects the cycle of operation from the given pre-programmed cycles. Each pre-programmed cycle may have any number of adjustable parameters, which may be input by the user or may be set by the controller. The controller may set the parameter according to default values, predetermined values, or responsive to conditions within the treating chamber.

SUMMARY OF THE INVENTION

The invention relates to a method of determining a fluffing state of laundry based on a determined temperature indicative of the surface of the laundry.

DESCRIPTION OF EMBODIMENTS OF THE INVENTION

Figure 1:
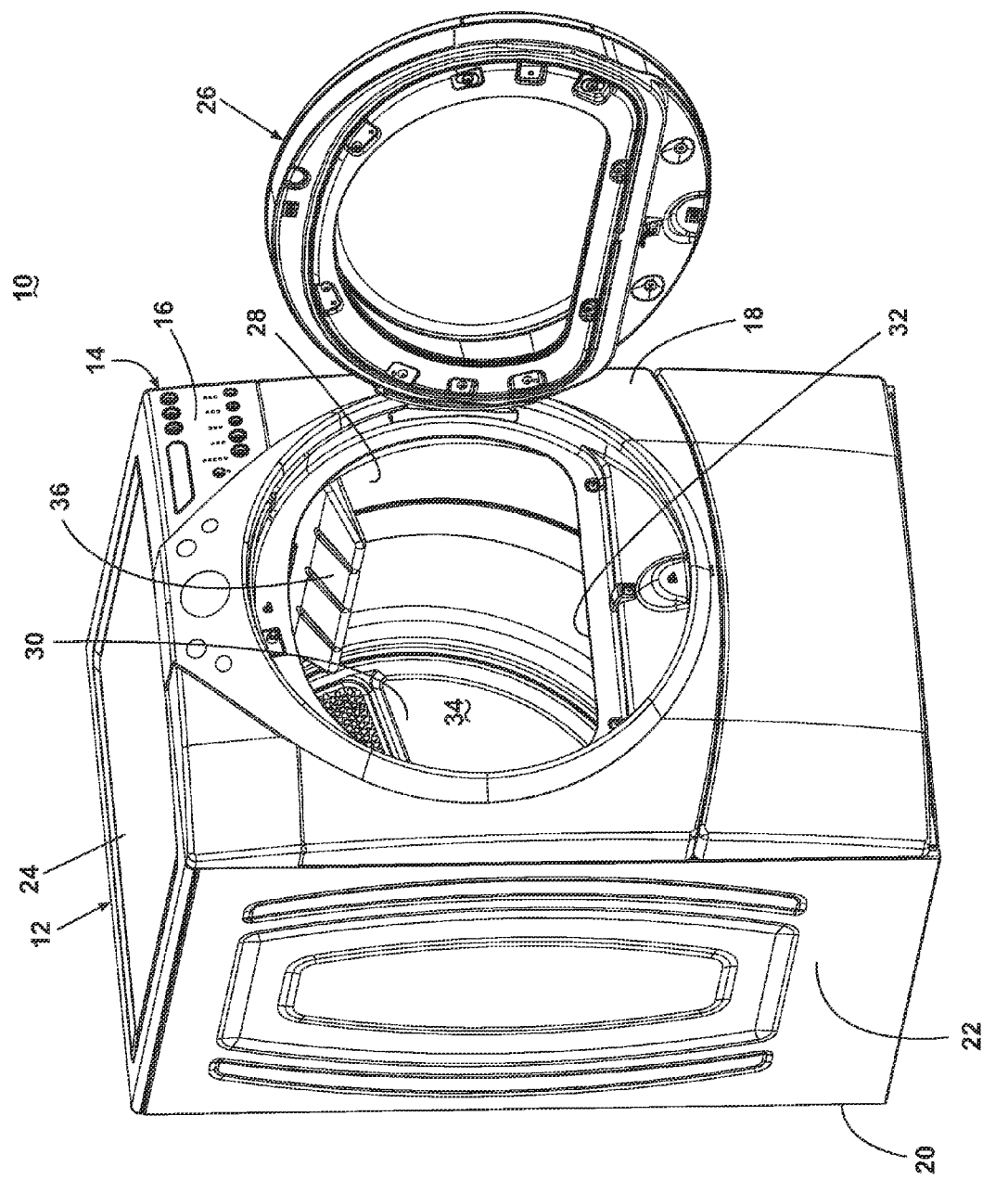
FIG. 1 is a front perspective view of a laundry treating appliance in the form of a clothes dryer with a treating chamber according to one embodiment of the invention.

FIG. 1 illustrates one embodiment of a laundry treating appliance in the form of a clothes dryer 10 according to the invention. While the laundry treating appliance is illustrated as a clothes dryer 10, the laundry treating appliance according to the invention may be any appliance which performs a cycle of operation on laundry, non-limiting examples of which include a horizontal or vertical axis clothes washer; a combination washing machine and dryer; a tumbling or stationary refreshing/revitalizing machine; an extractor; a non-aqueous washing apparatus; and a revitalizing machine. The clothes dryer 10 described herein shares many features of a traditional automatic clothes dryer, which will not be described in detail except as necessary for a complete understanding of the invention.

As illustrated in FIG. 1, the clothes dryer 10 may comprises a cabinet 12 in which is provided a controller 14 that may receive input from a user through a user interface 16 for selecting a cycle of operation and controlling the operation of the clothes dryer 10 to implement the selected cycle of operation.

The cabinet 12 may be defined by a front wall 18, a rear wall 20, and a pair of side walls 22 supporting a top wall 24. A door 26 may be hingedly mounted to the front wall 18 and may be selectively moveable between opened and closed positions to close an opening in the front wall 18, which provides access to the interior of the cabinet.

A rotatable drum 28 may be disposed within the interior of the cabinet 12 between opposing stationary rear and front bulkheads 30 and 32, which collectively define a treating chamber 34, for treating laundry, having an open face that may be selectively closed by the door 26. Examples of laundry include, but are not limited to, a hat, a scarf, a glove, a sweater, a blouse, a shirt, a pair of shorts, a dress, a sock, a pair of pants, a shoe, an undergarment, and a jacket. Furthermore, textile fabrics in other products, such as draperies, sheets, towels, pillows, and stuffed fabric articles (e.g., toys), may be dried in the clothes dryer 10.

The drum 28 may include at least one lifter 36. In most dryers, there are multiple lifters. The lifters 36 may be located along the inner surface of the drum 28 defining an interior circumference of the drum 28. The lifters 36 facilitate movement of the laundry within the drum 28 as the drum 28 rotates.

Figure 2:
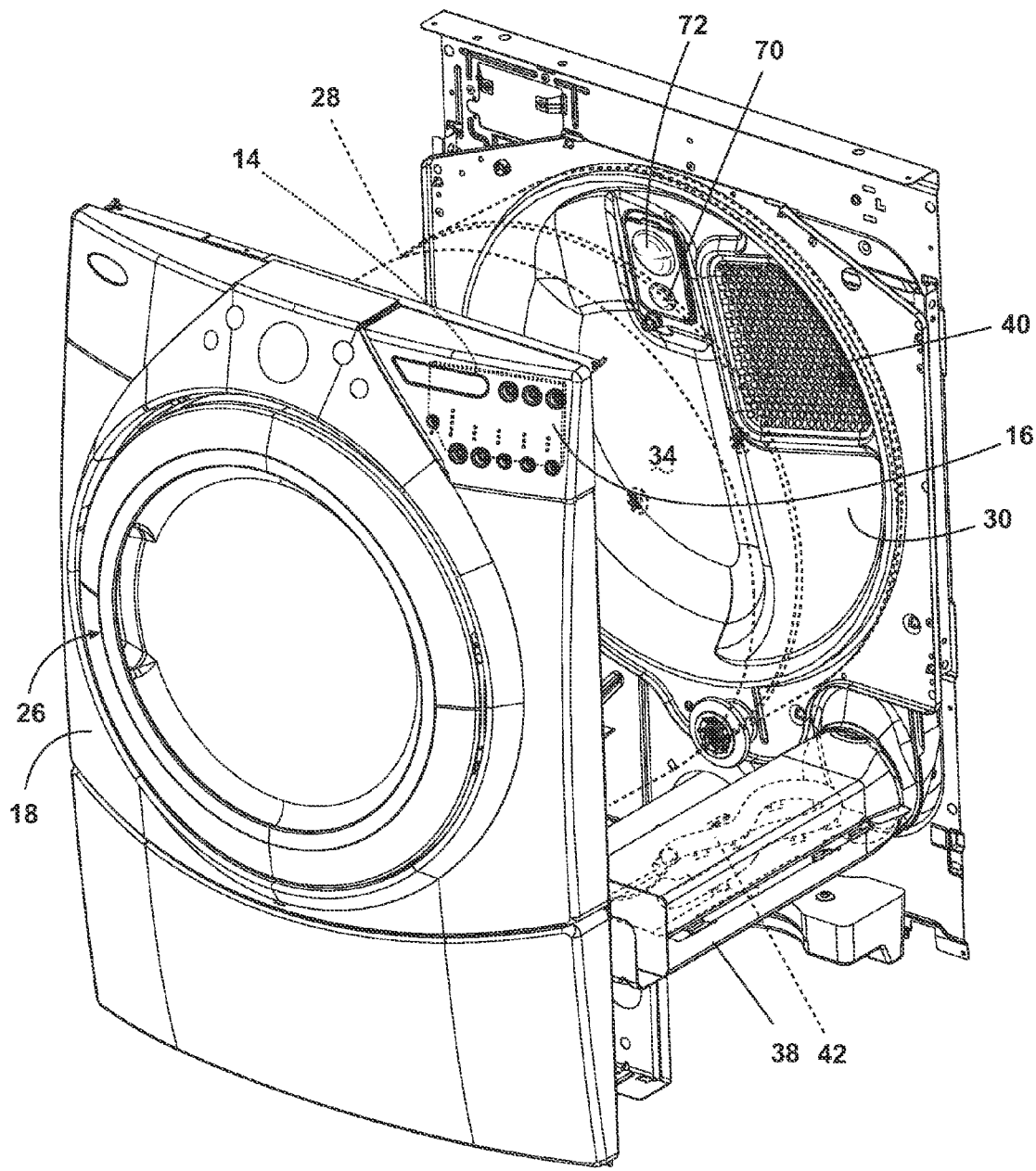
FIG. 2 is a partial perspective view of the dryer of FIG. 1 with portions of the cabinet removed for clarity according to one embodiment of the invention.

Still referring to FIG. 2, an air flow system for the clothes dryer 10 according to one embodiment of the invention will now be described. The air flow system supplies air to the treating chamber 34 and then exhausts air from the treating chamber 34. The supplied air may be heated or not. The air flow system may have an air supply portion that may be formed in part by an inlet conduit 38, which has one end open to the ambient air and another end fluidly coupled to an inlet grill 40, which may be in fluid communication with the treating chamber 34. A heating element 42 may lie within the inlet conduit 38 and may be operably coupled to and controlled by the controller 14. If the heating element 42 is turned on, the supplied air will be heated prior to entering the drum 28.

Figure 3:
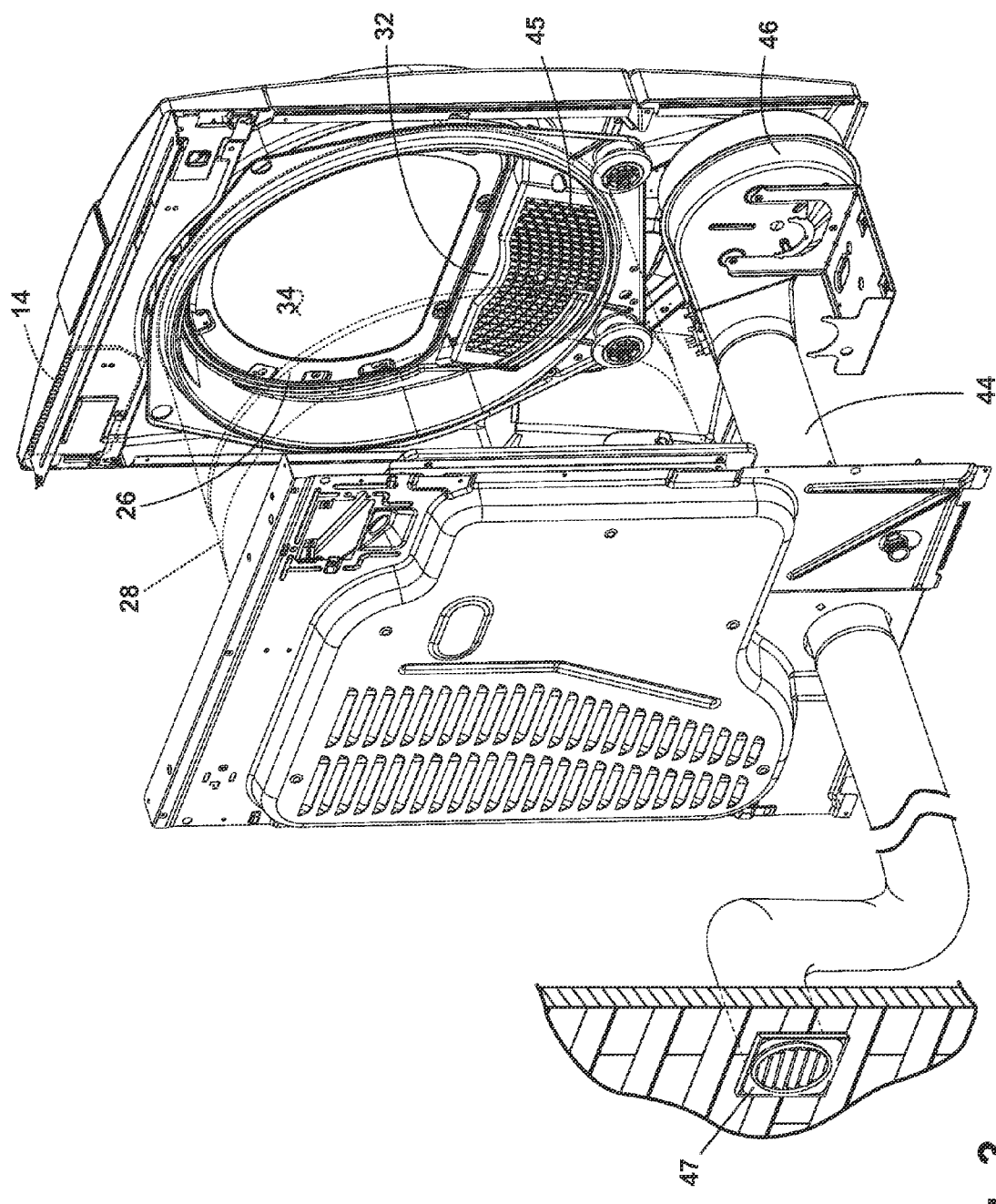
FIG. 3 is second partial perspective view of the dryer of FIG. 1 with portions of the cabinet removed for clarity according to one embodiment of the invention.

Referring to FIG. 3, the air supply system may further include an air exhaust portion that may be formed in part by an exhaust conduit 44 and lint trap 45, which are fluidly coupled by a blower 46. The blower 46 may be operably coupled to and controlled by the controller 14. Operation of the blower 46 draws air into the treating chamber 34 as well as exhausts air from the treating chamber 34 through the exhaust conduit 44. The exhaust conduit 44 may be fluidly coupled with a household exhaust duct 47 or exhausting the air from the drying chamber to the outside.

Figure 4:
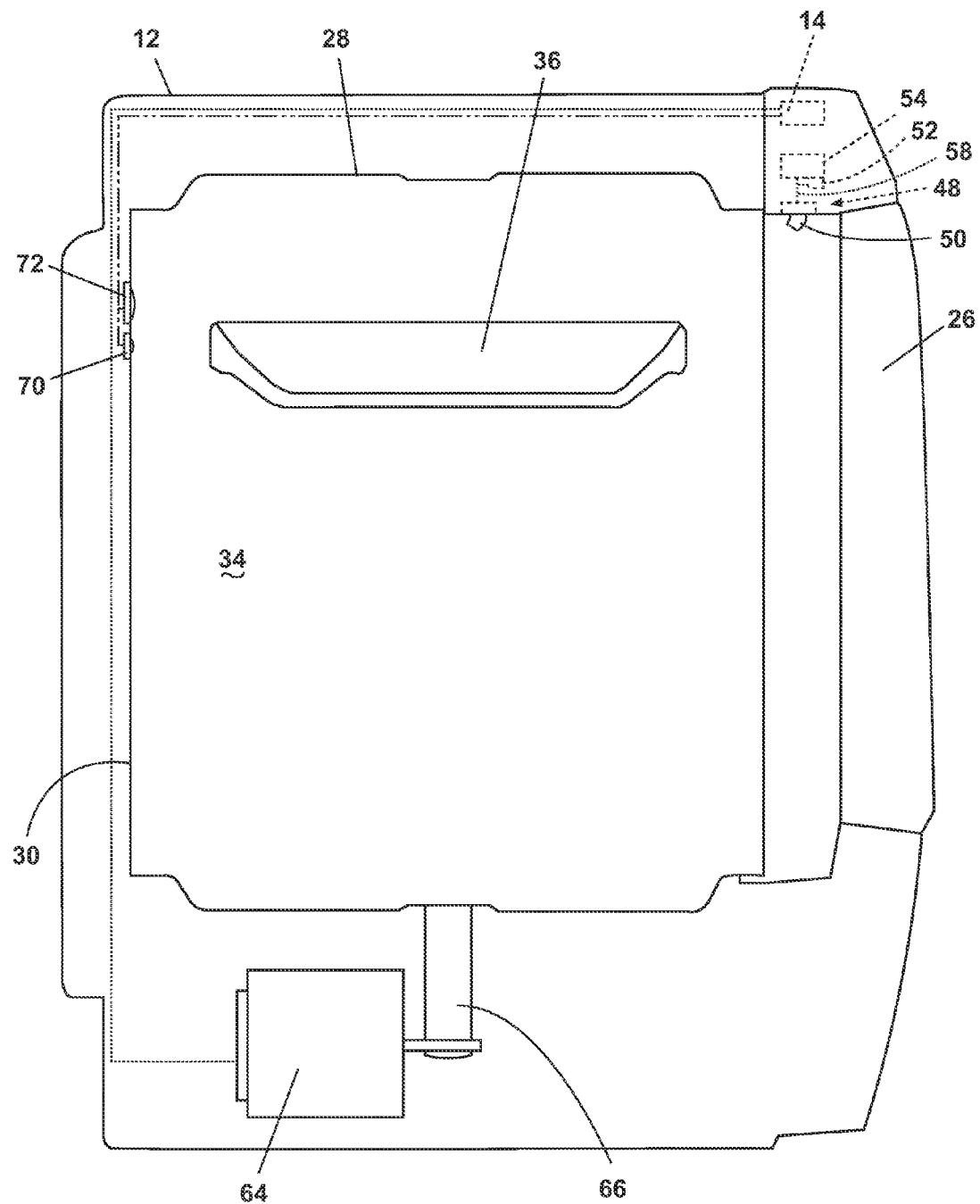
FIG. 4 is a cross-sectional, schematic side view of the dryer of FIG. 1 having an imaging system for imaging the treating chamber the dryer according to one embodiment of the invention.

Referring now to FIG. 4, the clothes dryer 10 may optionally have a dispensing system 48 for dispensing treating chemistries, including without limitation liquid or steam, into the treating chamber 34, and thus may be considered to be a dispensing dryer. The dispensing system 48 may include a reservoir 54 capable of holding treating chemistry and a dispenser 50 that fluidly couples with the reservoir 54 through a dispensing line 58. The treating chemistry may be delivered to the dispenser 50 from the reservoir 54 and the dispenser 50 may dispense the chemistry into the treating chamber 34. The dispenser 50 may be positioned to direct the treating chemistry at the inner surface of the drum 28 so that laundry may contact and absorb the chemistry, or to dispense the chemistry directly onto the laundry in the treating chamber 34. The type of dispenser 50 is not germane to the invention. A chemistry meter 52 may electronically couple, wired or wirelessly, to the controller 14 to control the amount of treating chemistry dispensed.

As is typical in a clothes dryer, the drum 28 may be rotated by a suitable drive mechanism, which is illustrated as a motor 64 and a coupled belt 66. The motor 64 may be operably coupled to the controller 14 to control the rotation of the drum 28 to complete a cycle of operation. Other drive mechanisms, such as direct drive, may also be used.

The clothes dryer 10 may also have a non-contact sensor 70 to determine the temperature or the amount of liquid present at the surface of the laundry. The non-contact sensor 70 may be any device capable of detecting emitted, absorbed, transmitted or reflected radiation indicative of the temperature of the surface of the laundry or the amount of liquid present at the surface of the laundry. The non-contact sensor 70 may also be an optical detector such as a CCD detector or a photomultiplier tube. The non-contact sensor 70 may capture either or both visible and non-visible radiation. An example of a suitable non-contact sensor 70 includes an infrared pyrometer or thermometer that detects the amount of infrared radiation emitted by an object.

In the context of an imaging device, the non-contact sensor 70 may include any optical sensor capable of capturing still or moving images, such as a thermal camera, wherein the image data contains information indicative of the temperature of the laundry. Examples of suitable cameras include a CMOS camera, a CCD camera, a digital camera, a video camera or any other type of device capable of capturing an image.

The non-contact sensor 70 may be located on either of the rear or front bulkhead 30, 32 or in the door 26. It may be readily understood that the location of the non-contact sensor 70 may be in numerous other locations depending on the particular structure of the dryer and the desired position for obtaining an image. There may also be multiple imaging devices, which may image the same or different areas of the treating chamber 34.

The clothes dryer 10 may also have an illumination source 72. The type of illumination source 72 may vary depending on the desired wavelength of emitted radiation, which may depend on the type of non-contact sensor 70. The illumination source 72 may emit light in the visible or non-visible spectrum. The wavelength of light emitted by the illumination source 72 may be selected such that the light emitted by the illumination source 72 and reflected, transmitted or absorbed by the load may be detected by the non-contact sensor 70 to determine one or more properties of the load. The illumination source 72 may be an incandescent light bulb, a mercury lamp, a halogen lamp, a laser, an LED or any other device capable of emitting radiation in the visible or non-visible spectrum.

The illumination source 72 may also be located behind the rear bulkhead 30 of the drum 28 such that the radiation shines through the holes of the air inlet grill 40. It is also within the scope of the invention for the clothes dryer 10 to have more than one illumination source 72. For example, an array of illumination sources 72 may be placed at multiple positions in either bulkhead 30, 32.

Figure 5:
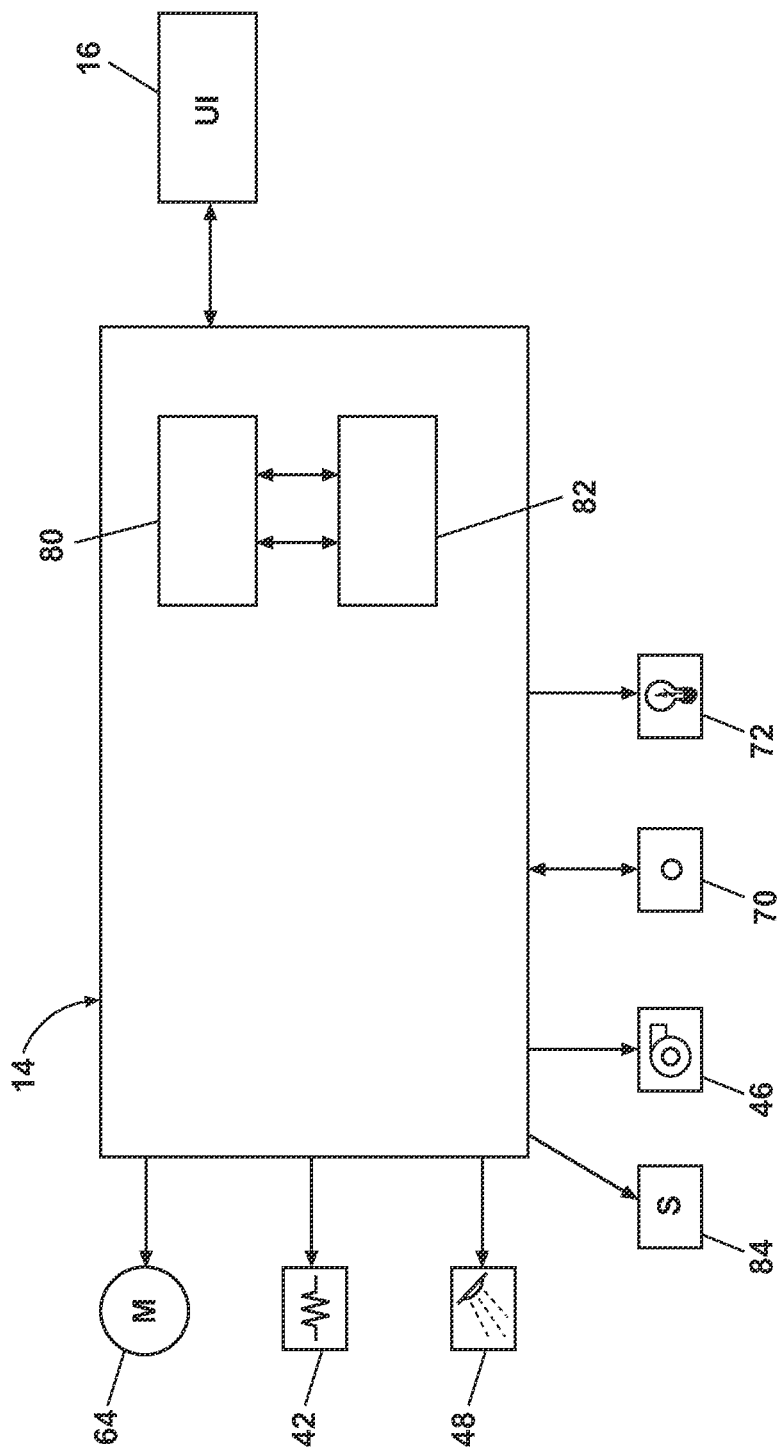
FIG. 5 is a schematic representation of a controller for controlling the operation of one or more components of the clothes dryer of FIG. 1 according to one embodiment of the invention.

As illustrated in FIG. 5, the controller 14 may be provided with a memory 80 and a central processing unit (CPU) 82. The memory 80 may be used for storing the control software that is executed by the CPU 82 in completing a cycle of operation using the clothes dryer 10 and any additional software. The memory 80 may also be used to store information, such as a database or table, and to store data received from the one or more components of the clothes dryer 10 that may be communicably coupled with the controller 14.

The controller 14 may be communicably and/or operably coupled with one or more components of the clothes dryer 10 for communicating with and controlling the operation of the component to complete a cycle of operation. For example, the controller 14 may be coupled with the heating element 42 and the blower 46 for controlling the temperature and flow rate through the treatment chamber 34; the motor 64 for controlling the direction and speed of rotation of the drum 28; and the dispensing system 48 for dispensing a treatment chemistry during a cycle of operation. The controller 14 may also be coupled with the user interface 16 for receiving user selected inputs and communicating information to the user.

The controller 14 may also receive input from various sensors 84, which are known in the art and not shown for simplicity. Non-limiting examples of sensors 84 that may be communicably coupled with the controller 14 include: a treating chamber temperature sensor, an inlet air temperature sensor, an exhaust air temperature sensor, a moisture sensor, an air flow rate sensor, a weight sensor, and a motor torque sensor.

The controller 14 may also be coupled with the non-contact sensor 70 and illumination source 72 to obtain information relating to one or more properties of the surface of the laundry load. This may include determining a temperature of the surface of the load or determining the amount of liquid present at the surface of the load. These properties may be used to determine a fluffing state of the laundry. Determining the temperature or the amount of liquid present at the surface of the load may include analyzing one or more sensor readings of the treating chamber 34. In this manner, the non-contact sensor 70 and illumination source 72 may provide a non-contact sensor for determining information regarding the surface of the laundry.

The sensor readings may be sent to the controller 14 and analyzed using analysis software stored in the controller memory 80 to determine a fluffing state of the laundry. The controller 14 may use the determined fluffing state to set one or more operating parameters to control the operation of at least one component with which the controller 14 is operably coupled to complete a cycle of operation.

A brief description regarding the fluffing state of laundry may be useful in understanding the invention. During a treating process, it is common for liquid to be disposed on the surface of the laundry. In many cases, the laundry will have liquid on the surface as well as the interior of the laundry. As the laundry dries, there will become a point where the surface is free from liquid. This point is commonly known as the fluffing state. That is, the fluffing state is when the surface is free of liquid regardless of whether there is liquid in the interior of the laundry. After reaching the fluffing state, the temperature of the laundry may begin to rise rapidly. The amount of liquid remaining in the laundry at the fluffing point is generally the amount of moisture that the laundry items may retain when stored at room temperature.

In the case of the clothes dryer 10, the controller 14 may use an indication of a fluffing state to set one or more parameters of a treating cycle including a cycle step time, a cycle time, a cycle temperature, a direction of drum 28 rotation, a drum 28 rotational speed, an air flow rate in the treating chamber 34, a type of treating chemistry and an amount of treating chemistry.

In the case of a clothes washing machine, the fluffing state may be used to determine the load distribution during a wash or spin cycle. One or more parameters including a cycle step time, a cycle time, a direction of drum rotation, a drum rotational speed, a direction of agitator rotation, an agitator rotational speed, a wash liquid fill level, a type of treating chemistry, an amount of treating chemistry and a time to dispense a treating chemistry may be set according to the determined load distribution.

The previously described clothes dryer 10 provides the structure necessary for the implementation of the method of the invention. Several embodiments of the method will now be described in terms of the operation of the clothes dryer 10. The embodiments of the method function to automatically determine the fluffing state of the laundry load and control the operation of the clothes dryer 10 based on the determined fluffing state.

The fluffing state of the laundry may be determined by using the non-contact sensor 70 to obtain one or more sensor readings over time of the contents of the drum 28 as it is rotating. The fluffing state of the laundry may then be used to control the operation of the clothes dryer 10.

Controlling the operation of the clothes dryer 10 based on the determined fluffing state may include setting at least one parameter of a cycle of operation including a cycle step time, a cycle time, a cycle temperature, a direction of drum 28 rotation, a drum 28 rotational speed, an air flow rate in a treating chamber 34, a type of treating chemistry, a time to dispense treating chemistry and an amount of treating chemistry to dispense.

Setting a cycle step time may include determining the duration of a cycle step within a cycle of operation or determining when to start or end a cycle step. This may include signaling the controller 14 to immediately transition from one cycle step to another or setting a time at which to transition from one step to another within a given operating cycle. Examples of cycle steps include rotation with heated air, rotation without heated air, treatment dispensing and a wrinkle guard step.

Setting a cycle time may include determining the duration of a cycle of operation or determining when to start or end a cycle of operation. This may include signaling the controller 14 to immediately start or end a cycle of operation or setting a time at which to start or end a cycle of operation.

For laundry treating appliances other than clothes dryers, parameters of a cycle of operation that may be set based on the determined fluffing state may also include a rotational speed of an agitator, a direction of agitator rotation, and a wash liquid fill level.

Figure 6:
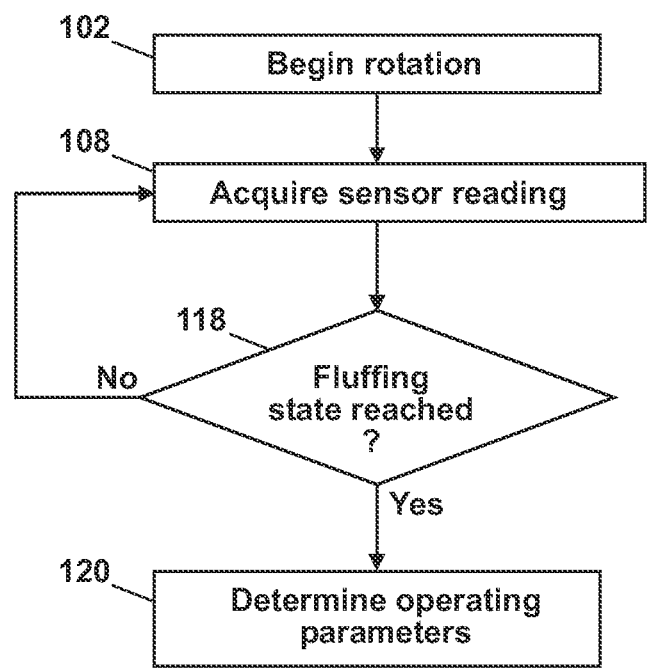
FIG. 6 is a flow chart illustrating a method for capturing and analyzing images of the treating chamber to determine a fluffing state according to a second embodiment of the invention.

Referring to FIG. 6, a flow chart of one method 100 of determining the fluffing state of a load of laundry is shown in accordance with the present invention. The fluffing state determining method 100 may be executed by the controller 14 during a drying or treatment cycle of the clothes dryer 10. The sequence of steps depicted is for illustrative purposes only, and is not meant to limit the fluffing determining method 100 in any way as it is understood that the steps may proceed in a different logical order or additional or intervening steps may be included without detracting from the invention.

The method 100 is discussed in the context of a non-contact sensor 70 in the form of an infrared thermometer capable of detecting the infrared radiation emitted by the laundry and determining a temperature of the laundry based on the emitted infrared radiation. It is within the scope of the invention for the non-contact sensor 70 to be in the form of a thermal camera capable of capturing an image of the load wherein each pixel in the image may be translated into a value indicative of the temperature of the item at that point on the item's surface.

The method 100 starts with assuming that the user has loaded the clothes dryer 10 with one or more articles to form the laundry load and closed the door 26. The method 100 may be initiated automatically when the user closes the door 26 or at the start of a user selected operating cycle.

In the step 102 the rotation of the drum 28 is initiated; the speed of rotation of the drum 28 may be increased until it reaches a predetermined speed of rotation. The predetermined speed of rotation may be determined by the controller 14 based on the selected operating cycle and the operating parameter settings. When the drum speed reaches the predetermined speed, the non-contact sensor 70 may take a sensor reading. Alternatively, the sensor reading may be initiated after a predetermined amount of time has elapsed or after a predetermined step in a cycle of operation.

In step 108, the non-contact sensor 70 may acquire a single temperature reading or multiple temperature readings. If the non-contact sensor 70 acquires multiple temperature readings, the temperature readings may be averaged before being communicated with the controller 14. The temperature reading acquired in step 108 may be sent to the controller 14 for analysis in step 110 using software that is stored in the memory 80 of the controller 14. It is also within the scope of the invention for the non-contact sensor 70 to have a memory and a microprocessor for storing information and software and executing the software, respectively. In this manner, the non-contact sensor 70 may analyze the temperature data and communicate the results of the analysis with the controller 14.

Several methods may be used in step 118 to determine if the temperature data indicates a fluffing state. In the simplest form, the method may involve determining that the temperature reading acquired in step 108 is above a predetermined threshold value, indicating the existence of a fluffing state.

Alternatively, multiple temperature readings may be acquired over time in step 108 and stored in a database of load temperatures in a memory accessible by the controller 14 such as the controller memory 80. The stored temperature data may be used by the controller 14 to determine when the load has entered the fluffing state. This may include comparing the determined temperatures of the load between consecutive sensor readings to determine if a change in the temperature of the load is greater than a predetermined threshold. Alternatively, the rate of change of the temperature of the load for multiple readings may be determined. The change or rate of change in temperature may then be used by the controller 14 to determine that a fluffing state has been reached.

If it is determined that a fluffing state has been reached in step 118, the controller 14 may control the operation of the clothes dryer 10 based on the determined fluffing state in step 120. This may include setting at least one parameter of a cycle of operation including a cycle step time, a cycle time, a cycle temperature, a direction of drum 28 rotation, a drum 28 rotational speed, an air flow rate in a treating chamber 34, a type of treating chemistry, a time to dispense a treating chemistry and an amount of treating chemistry to dispense.

For example, if it is determined that a fluffing state has been reached, the controller 14 may turn off the heating element 42 and set the blower 36 and motor 64 to continue the flow of air through the treating chamber 34 and rotation of the drum 28 for a predetermined amount of time prior to ending the cycle of operation. In another example, once the fluffing state has been reached, the controller 14 may control the dispensing system 48 to dispense an anti-wrinkle treatment and set a time for ending the cycle of operation.

In addition to setting one or more parameters of a cycle of operation based on the determined fluffing state, the controller 14 may also use information received from one or more sensors 84. For example, an exhaust air temperature sensor may register a rise in the exhaust temperature indicating that less water is being evaporated from the load. In another example, a contact moisture sensor may be used to determine that little or no moisture is being removed from the load. The data from these types of sensors may be used in combination with the data obtained from the imaging device 70 for confirming the determination of the imaging system regarding the presence of a fluffing state. Additionally, these types of sensor may be used to initiate the imaging system for determining the fluffing state of the load.

If a fluffing state has not been reached, the steps 102 through 118 may be repeated until the controller 14 determines that a fluffing state has been reached.

The method 100 illustrated in FIG. 6 may also be used with a non-contact sensor 70 capable of detecting the amount of radiation absorbed or reflected by the laundry load to determine the amount of liquid present at the surface of the fabric of the laundry load. The amount of liquid present at the surface of the load may be used by the controller 14 to determine a fluffing state and control the operation of the clothes dryer 10 based on the determined fluffing state. For example, the amount of infrared radiation absorbed by the laundry load may be proportional to the amount of liquid present at the surface of the load.

According to this embodiment of the invention, the non-contact sensor 70 would be used in combination with an illumination source 72 capable of emitting infrared radiation. The illumination source 72 is placed within the treating chamber 34 opposite the non-contact sensor 70 such that the imaging device may 70 detect the amount of infrared radiation absorbed by the laundry.

A fluffing state corresponds to a state in which generally all of the liquid on the surface of the fabric of the load has evaporated and only the liquid internal to the fabric structure remains. Therefore, determining the amount of liquid associated with the fabric of the load may be used to determine when the load has entered a fluffing state.

Steps 102 through 108 of method 100 as illustrated in FIG. 6 may be used to acquire one or more sensor readings relating to the absorption of infrared radiation by the laundry. In step 108, the non-contact sensor 70 may acquire a single absorption reading or multiple absorption readings. If the non-contact sensor 70 acquires multiple absorption readings, the absorption readings may be averaged before being communicated with the controller 14. The one or more absorption readings acquired in step 108 may be sent to the controller 14 for analysis using software that is stored in the memory 80 of the controller 14. It is also within the scope of the invention for the non-contact sensor 70 to have a memory and a microprocessor for storing information and software and executing the software, respectively. In this manner, the non-contact sensor 70 may analyze the absorption data and communicate the results of the analysis with the controller 14.

Several methods may be used in step 118 to determine if the absorption data indicates a fluffing state. In the simplest form, the method may involve determining that a single absorption reading or that an averaged absorption reading acquired in step 108 is above a predetermined threshold value, indicating the existence of a fluffing state. The absorption readings corresponding to an amount of liquid on the surface of the load may be determined empirically and stored in a database or look-up table accessible by the controller 14. The acquired sensor reading may then be located in a table of absorption values and corresponding liquid values to determine the amount of liquid present at the surface of the load.

Alternatively, multiple absorption readings may be acquired over time in step 108 and stored in a database of load absorption values in a memory accessible by the controller 14 such as the controller memory 80. The stored absorption data may be used by the controller 14 to determine when one or more items of the load has entered the fluffing state. This may include comparing the determined absorption of the load between consecutive sensor readings to determine if a change in absorption of the load is greater than a predetermined threshold. Alternatively, the rate of change of the absorption of the load for multiple readings may be determined. The change or rate of change in temperature may then be used by the controller 14 to determine that a fluffing state has been reached.

If it is determined that a fluffing state has been reached in step 118, the controller 14 may control the operation of the clothes dryer 10 based on the determined fluffing state in step 120 as described previously. This may include setting at least one parameter of a cycle of operation including a cycle step time, a cycle time, a cycle temperature, a direction of drum 28 rotation, a drum 28 rotational speed, an air flow rate in a treating chamber 34, a type of treating chemistry, a time to dispense a treating chemistry and an amount of treating chemistry to dispense.

All of the embodiments of the invention have the benefit of determining when the laundry reaches the fluffing state, which has not previously been possible. Most previous dryers use exhaust air temperature to determine when the laundry is dry. The traditional method was to monitor the exhaust air temperature profile, which has three distinct phases: an initial ramp, a plateau, and a final ramp. The initial ramp was indicative of the bringing the exhaust air up to temperature. The plateau was indicative of the heat evaporating the liquid in the laundry, which requires a phase change from liquid to vapor theat kept the temperature generally constant or having a steady increase. Once all of the liquid was evaporated, the heat was no longer used to evaporate liquid and was passed through to the outlet, there is a sudden increase in the outlet air temperature as indicated by the final ramp. The inflection point between the plateau and final ramp has been used to indicate that no further drying is needed and the heat was shut off while the fan continued to pull air through the laundry until cool.

The prior exhaust air temperature method for determining dryness is not capable of detecting when the laundry is in a fluffing state because the inflection point occurs only after all of the liquid is evaporated from the clothes, which includes liquid on the surface of the laundry as well as liquid on the interior of the laundry, whereas the fluffing state is concerned only with the removal of liquid from the surface while permitting liquid to reside on the interior. In fact, the fluffing state is passed by the time the inflection point is reached.

It is desirable to detect the fluffing state as it is considered by many to be the ideal time to stop the addition of heat as the resulting laundry will not be bone dry and will contain some residual liquid. Drying laundry until it is bone dry may be detrimental to the longevity of many fabrics. The presence of residual moisture provides for easier ironing and post drying handling.

While the invention has been specifically described in connection with certain specific embodiments thereof, it is to be understood that this is by way of illustration and not of limitation. Reasonable variation and modification are possible within the scope of the forgoing disclosure and drawings without departing from the spirit of the invention which is defined in the appended claims. For example, the sequence of steps depicted in each method described herein is for illustrative purposes only, and is not meant to limit the disclosed methods in any way as it is understood that the steps may proceed in a different logical order or additional or intervening steps may be included without detracting from the invention.

What is claimed is:

1. A laundry treating appliance for treating laundry in accordance with a treating cycle of operation, comprising:
   a treating chamber;
   a non-contact temperature sensor configured to repeatedly generate temperature data representative of at least a portion of the laundry in the treating chamber; and
   a controller operably coupled to the temperature sensor and configured to determine a fluffing state of the laundry, where a surface of the laundry is free of liquid, from the temperature data and continue the treating cycle of operation and take an action based on the determined fluffing state, the action comprising: setting at least one parameter of a treating cycle of operation, wherein the at least one parameter comprises a cycle step within a cycle of operation, a cycle temperature, a direction of drum rotation, an air flow rate of heated air flowing through the treating chamber, a direction of agitator rotation, an agitator rotational speed, a wash liquid fill level, a type of treating chemistry to dispense, a time to dispense a treating chemistry, an amount of treating chemistry to dispense, or combinations thereof; and
   wherein the controller is further configured to end the treating cycle of operation subsequent to the taking an action.

2. The laundry treating appliance of claim 1 wherein the controller is further configured to determine an end of the treating cycle of operation after determining the fluffing state of the laundry.

3. The laundry treating appliance of claim 1 wherein the setting a cycle step comprises selecting the type of cycle of operation.

4. The laundry treating appliance of claim 1 wherein the controller is further configured to determine an end of at least a cycle step of the treating cycle of operation after determining the fluffing state of the laundry.

5. The laundry treating appliance of claim 1 wherein the cycle step of the treating cycle of operation comprises a heating step, an air flow step, a dispensing step, or a rotational step.

6. The laundry treating appliance of claim 1, further comprising a heating element to supply heated air to the treating chamber and wherein ending the treating cycle of operation comprises turning the heating element off to supply unheated air to the treating chamber.

7. The laundry treating appliance of claim 1 wherein the non-contact temperature sensor is configured to determine a surface temperature of at least a portion of the laundry.

8. The laundry treating appliance according to claim 1 wherein the non-contact temperature sensor comprises a thermal imaging device.

9. The laundry treating appliance according to claim 1 wherein the controller is further configured to initially select the treating cycle of operation based on the temperature data.

10. The laundry treating appliance according to claim 1, further comprising a dispensing system for dispensing a treating chemistry into the treating chamber.

11. The laundry treating appliance according to claim 10 wherein the dispensing system is operably coupled to the controller and wherein at least one of a type of treating chemistry, a time to dispense a treating chemistry, or an amount of treating chemistry is selected based on the temperature data.

12. The laundry treating appliance of claim 1, further comprising at least one of the following sensors operably coupled to the controller and providing a corresponding input to the controller: a treating chamber temperature sensor, an inlet air temperature sensor, an exhaust air temperature sensor, a moisture sensor, an air flow rate sensor, a weight sensor, or a motor torque sensor.

* * * * *